(12) United States Patent
Folk

(10) Patent No.: US 8,986,225 B2
(45) Date of Patent: Mar. 24, 2015

(54) GUIDEWIRE

(75) Inventor: Christopher Folk, Los Angeles, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/564,784

(22) Filed: Aug. 2, 2012

(65) Prior Publication Data

US 2014/0039350 A1      Feb. 6, 2014

(51) Int. Cl.
  *A61M 25/00*      (2006.01)
  *A61M 25/09*      (2006.01)

(52) U.S. Cl.
  CPC ............... *A61M 25/09041* (2013.01); *A61M 2025/09116* (2013.01); *A61M 2025/09175* (2013.01)
  USPC ........................................ 600/585

(58) Field of Classification Search
  CPC ....... A61B 1/01; A61M 25/09; A61M 25/092
  USPC .................. 600/433, 434, 585; 604/164.13
  See application file for complete search history.

(56) References Cited

U.S. PATENT DOCUMENTS

| | | | |
|---|---|---|---|
| 3,625,200 A | 12/1971 | Muller | |
| 4,554,929 A | 11/1985 | Samson et al. | |
| 4,921,482 A | 5/1990 | Hammerslag et al. | |
| 5,108,368 A | 4/1992 | Hammerslag et al. | |
| 5,308,324 A | 5/1994 | Hammerslag et al. | |
| 5,368,592 A * | 11/1994 | Stern et al. | 606/33 |
| 5,833,632 A | 11/1998 | Jacobsen et al. | |
| 6,165,139 A | 12/2000 | Damadian | |
| 6,290,715 B1 | 9/2001 | Sharkey et al. | |
| 6,302,865 B1 | 10/2001 | Urick | |
| 7,118,539 B2 | 10/2006 | Vrba et al. | |
| 7,449,002 B1 | 11/2008 | Wenstad | |
| 7,892,186 B2 | 2/2011 | Soukup et al. | |
| 8,046,049 B2 | 10/2011 | Govari et al. | |
| 8,070,693 B2 | 12/2011 | Ayala et al. | |
| 8,114,017 B2 * | 2/2012 | Bacher | 600/204 |
| 8,287,469 B2 | 10/2012 | Stefanchik et al. | |

(Continued)

FOREIGN PATENT DOCUMENTS

| | | |
|---|---|---|
| RU | 2074010 C1 | 2/1997 |
| RU | 2329071 C2 | 7/2008 |

(Continued)

OTHER PUBLICATIONS

European Search Report from corresponding EP application 13177078.6 mailed Dec. 10, 2013 (3pages).

(Continued)

*Primary Examiner* — Max Hindenburg
*Assistant Examiner* — Jonathan M Foreman
(74) *Attorney, Agent, or Firm* — Elizabeth A. O'Brien, Esq.

(57) ABSTRACT

A guidewire for use in a medical procedure includes an elongate guide member dimensioned for insertion within a body vessel of a subject. The guide member includes an elongate body segment and a leading tip segment. The elongate body segment defines a longitudinal opening, and the leading tip segment is adapted and dimensioned to articulate relative to the elongate body segment about a single axis. A control element extends through the longitudinal opening of the elongate body segment and is longitudinally movable through manual manipulation of a clinician to cause corresponding articulating movement of the leading tip segment.

28 Claims, 6 Drawing Sheets

(56) References Cited

U.S. PATENT DOCUMENTS

| | | |
|---|---|---|
| 2003/0109810 A1 | 6/2003 | Brennan et al. |
| 2003/0233056 A1 | 12/2003 | Saadat et al. |
| 2004/0102719 A1 | 5/2004 | Keith et al. |
| 2004/0143197 A1 | 7/2004 | Soukup et al. |
| 2004/0181249 A1 | 9/2004 | Torrance et al. |
| 2006/0025705 A1 | 2/2006 | Whitaker et al. |
| 2006/0111609 A1 | 5/2006 | Bacher |
| 2006/0241519 A1 | 10/2006 | Hojeibane et al. |
| 2007/0123804 A1* | 5/2007 | Ayala et al. .......... 600/585 |
| 2007/0219465 A1 | 9/2007 | Cedro et al. |
| 2008/0221482 A1 | 9/2008 | Mondry et al. |
| 2009/0156995 A1 | 6/2009 | Martin et al. |

FOREIGN PATENT DOCUMENTS

| | | |
|---|---|---|
| WO | 2006057702 A2 | 6/2006 |
| WO | 2007061702 A2 | 5/2007 |

OTHER PUBLICATIONS

Notification of First Office Action, and translation thereof, from counterpart Chinese Patent Application No. 201310332925.1, dated Dec. 15, 2014, 14 pages.

Notice of Preliminary Rejection, and translation thereof, from counterpart Korean Patent Application No. 10-2013-91325, dated Oct. 28, 2014, 9 pages.

Notice of Reasons for Rejection, and translation thereof, from counterpart Japanese Patent Application No. 2013-156487, mailed Oct. 2, 2014, 7 pages.

Office Action, and translation thereof, from counterpart Russian Patent Application No. 2013134196, dated Aug. 22, 2014, 11 pages.

Examination Report from counterpart European Patent Application No. 13177078.6, dated Nov. 17, 2014, 4 pages.

* cited by examiner

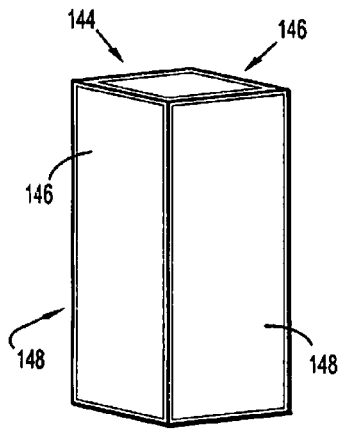 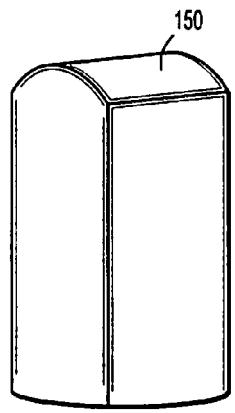 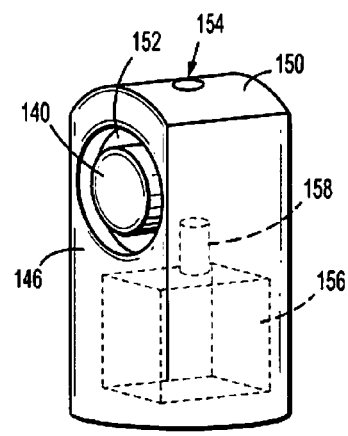
FIG. 4A  FIG. 4B  FIG. 4C
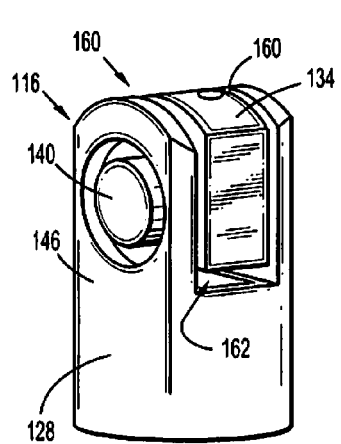 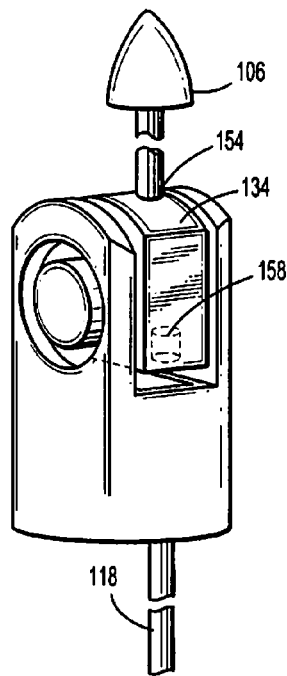 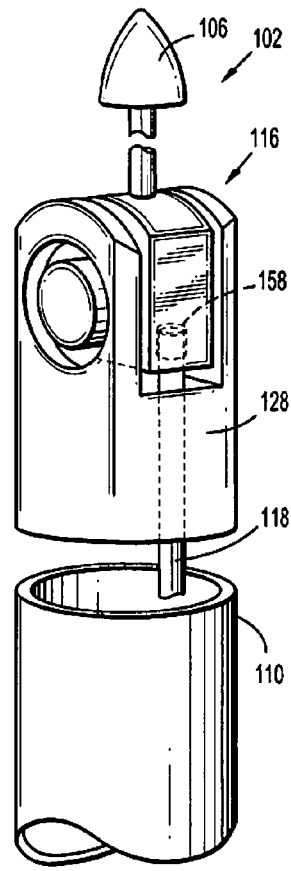
FIG. 4D  FIG. 4E  FIG. 4F

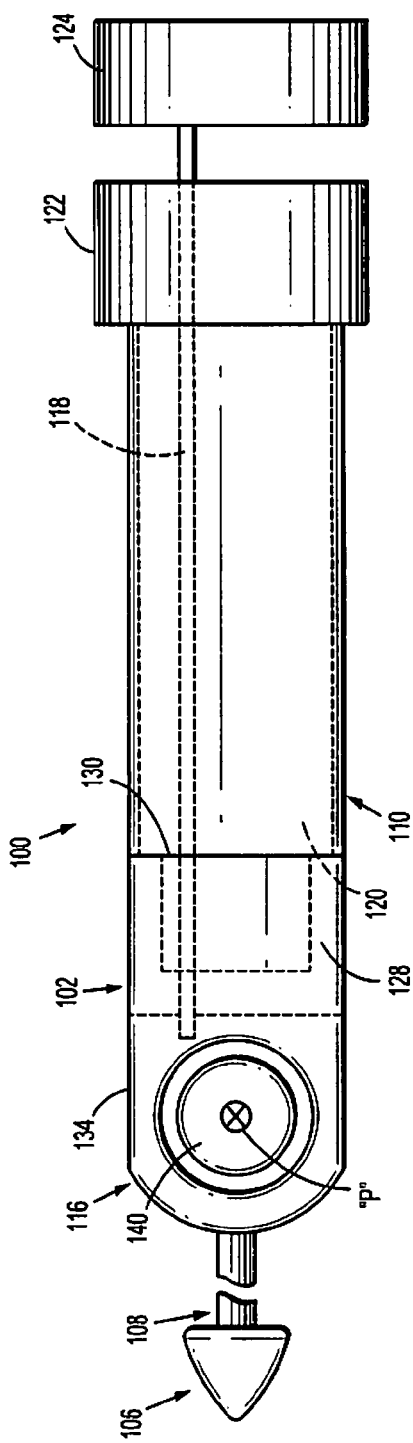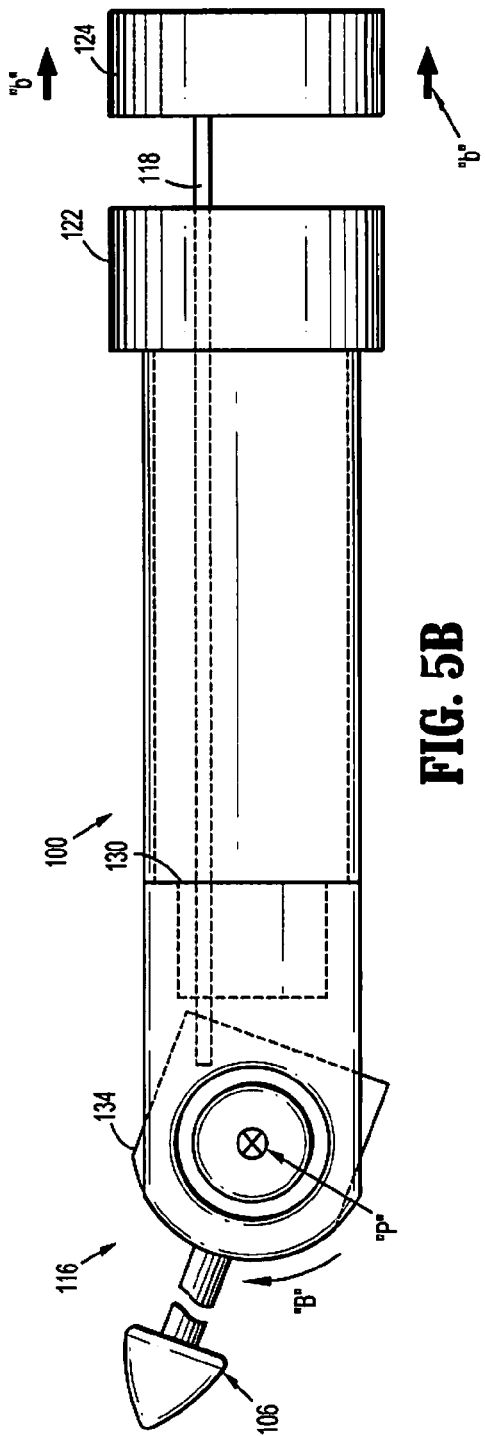

GUIDEWIRE

BACKGROUND

1. Technical Field

The present disclosure generally relates to medical devices for facilitating diagnostic and/or therapeutic procedures. In particular, the disclosure relates to a guidewire for assisting in placement of an intravascular device within the neurovasculature.

2. Description of Related Art

Guidewires are commonly used in medical procedures to assist in the advance and proper positioning of a catheter or other medical device in lumens, vessels, or other cavities of the body. Neurovascular procedures utilizing guidewires include the imaging and treatment of aneurysms, arteriovenous malformations (AVM), and ischemic stroke. The effectiveness of an intravascular guidewire in advancing through tortuous neurovasculature without undesired deformation or kinking is dependent upon a number of factors and design considerations. These factors include, inter-alia, the material(s) of fabrication of the guidewire, guidewire dimensions and intended use. Generally, a balance must be achieved to provide the required torsional, lateral, tensile and/or column strengths to enable easy and precise manipulation and steerability in the tortuous vasculature. Guidewires for neurovascular intravascular procedures face additional challenges due to the relatively small diameter required to navigate through the narrow and remote locations of the neurovasculature. As a result, the movements of the guidewire induced by a clinician may not always result in the positioning of the guidewire at a desired orientation relative to the vascular tissue.

SUMMARY

Accordingly, the present disclosure is directed to a guidewire capable of accessing distal reaches of the vasculature, including the neurovasculature. The guidewire includes a leading tip segment at a leading end thereof, which may be selectively controlled by a clinician to facilitate steering the guidewire through these tortuous regions.

In accordance with one embodiment of the present disclosure, a guidewire for use in a medical procedure includes an elongate guide member dimensioned for insertion into a body vessel of a subject. The elongate guide member defines a longitudinal axis and has leading and trailing ends. The elongate guide member includes an elongate body segment and a leading tip segment. The elongate body segment defines a longitudinal opening or lumen, and the leading tip segment is adapted and dimensioned to articulate relative to the elongate body segment about a single axis. A control element extends through the longitudinal opening of the elongate body segment and is operatively coupled to the leading tip segment such that the control element is longitudinally movable through manual manipulation of a clinician to cause corresponding articulating movement of the leading tip segment.

The guide member may include an articulation joint for coupling the leading tip segment to the elongate body segment. The articulation joint may include a base coupled to the elongate body segment and a pivoting member mounted to the base. The pivoting member may be coupled to the leading tip segment and to the control element, and the pivoting member may be adapted to pivot relative to the base and about the single axis in response to longitudinal movement of the control element to thereby cause corresponding pivoting movement of the leading tip segment. The control element may be connected to the pivoting member at a location spaced from the single axis. The pivoting member may define an off-center bore spaced from the single axis for receiving a leading end of the control element. The pivoting member may be mounted to a pivot boss, and the pivot boss may extend generally along the single axis and be coupled to the base.

In accordance with a further aspect of the disclosure, an intravascular guidewire includes an elongate guide member dimensioned for insertion within a body vessel of a subject. The elongate guide member defines a longitudinal axis and has leading and trailing ends. The elongate guide member includes an elongate body segment and a leading tip segment, and the leading tip segment is adapted and dimensioned to pivot relative to the elongate body segment. A single control element is operatively coupled to the leading tip segment. The control element is longitudinally movable through manual manipulation of a clinician to cause corresponding pivoting movement of the leading tip segment.

The leading tip segment may be adapted to pivot about a single pivot axis. The control element may be operatively coupled to the leading tip segment at a location radially spaced from the single pivot axis.

The guidewire may include an articulation joint for coupling the leading tip segment to the elongate body segment. The articulation joint may be dimensioned and adapted to enable pivotal movement of the leading tip segment relative to the elongate body segment. The articulation joint may include a pivoting member that is coupled to the leading tip segment and to the control element. The pivoting member may be adapted to pivot about the single axis in response to longitudinal movement of the control element to thereby cause corresponding pivoting movement of the leading tip segment. The articulation joint may also include a base that is coupled to the elongate body segment and has the pivoting member pivotally mounted thereto.

The elongate body segment may define a longitudinal opening, and the control element may be at least partially disposed within the longitudinal opening and adapted for reciprocal longitudinal movement therewithin to cause corresponding pivotal movement of the leading tip segment. The guidewire may further include a handle coupled to a trailing end of the control element for selectively longitudinally moving the control element.

BRIEF DESCRIPTION OF THE DRAWINGS

Embodiments of the present disclosure will be readily appreciated by reference to the drawings wherein:

FIGS. 4A-4F are perspective views of the elongate guide member of FIG. 2 in various stages of assembly;

FIG. 5A is a schematic view of the guidewire of FIG. 2 illustrating a leading tip segment of the guidewire in an aligned configuration;

FIG. 5B is a schematic view of the guidewire of FIG. 2 illustrating the leading tip segment of the guidewire in an articulated configuration.

DESCRIPTION

Figure 1:
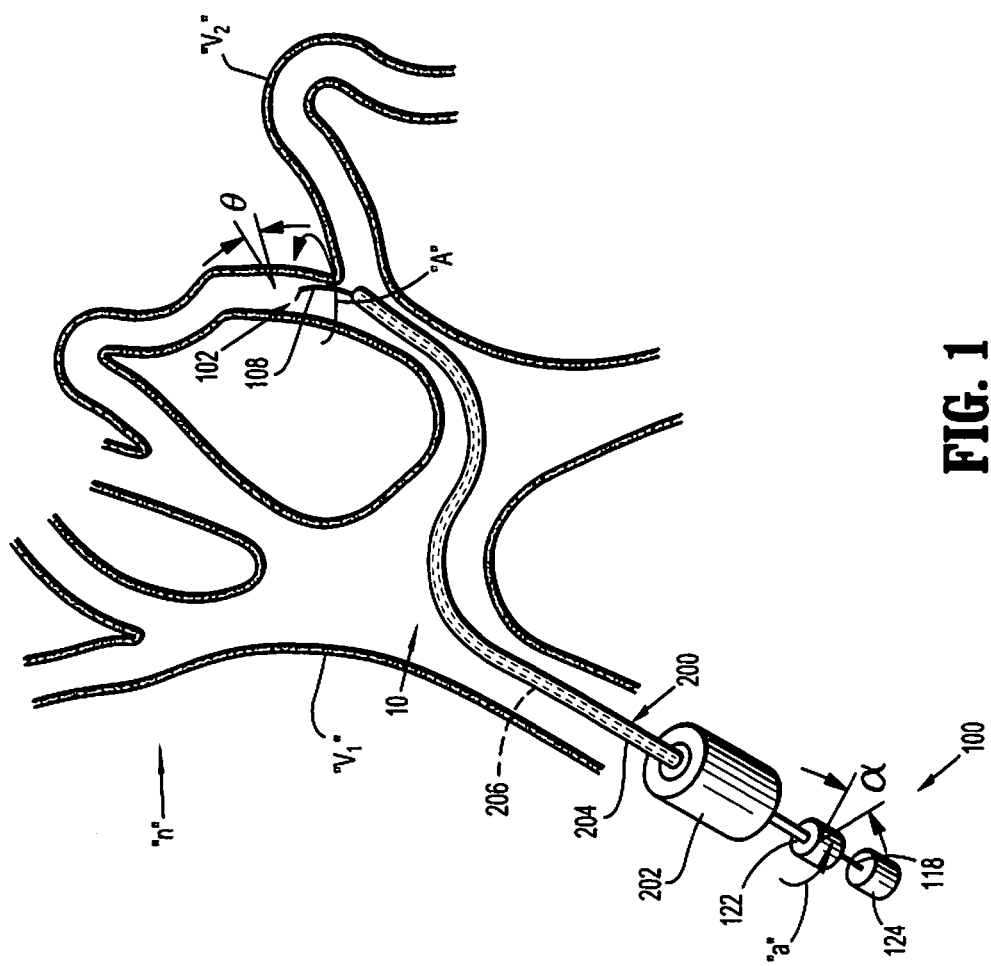
FIG. 1 is a perspective view of a guidewire and catheter in use within the vasculature of a patient in accordance with the principles of the present disclosure.

In the following description, the terms "proximal" and "distal" as used herein refer to the relative position of the guidewire in a lumen. The "proximal" or "trailing" end of the guidewire is the guidewire segment extending outside the body closest to the clinician. The "distal" or "leading" end of the guidewire is the guidewire segment placed farthest into a body lumen from the entrance site.

The guidewire of the present disclosure has particular application in neurovascular procedures, but may be used in any interventional, diagnostic, and/or therapeutic procedure including coronary vascular, peripheral vascular, and gastrointestinal applications in addition to a neurovascular application. The guidewire may be used in a variety of procedures including guiding other devices, such as catheters, stents, and/or balloons to target sites within a patient's body.

In the figures below, the full length of the guidewire is not shown. The length of the guidewire can vary depending on the type of interventional procedure, though typically it ranges in length from 30 to 400 centimeters (cm). Common lengths of guidewires for coronary, peripheral and neurovascular interventions may range from 170 to 300 cm. These lengths permit the use of the guidewire with standardized rapid exchange or over-the-wire catheter systems.

In accordance with one application of the present disclosure, the maximum outer diameter of the guidewire ranges from about 0.008 inches to about 0.018 inches. These diameters are standard for guidewires used in neurovascular procedures. The diameter of the guidewire may remain relatively constant over a major body portion or length of the guidewire; however, the leading or distal end may exhibit a generally tapered or narrowed configuration with respect to the major body portion.

The various embodiments of the disclosure will now be described in connection with the drawing figures. It should be understood that for purposes of better describing the disclosure, the drawings may not be to scale. Further, some of the figures include enlarged or distorted portions for the purpose of showing features that would not otherwise be apparent.

Referring now to FIG. 1, a tortuous vasculature such as within the neurovascular space "n" is illustrated. For illustrative purposes, a tortuous path or a tortuous region within, e.g., the neurovascular space "n", includes large vasculature "v1" and smaller branch vessels "v2" which branch or extend from more proximal vessels at various angles, including up to 90 degrees or even greater than 90 degrees.

In FIG. 1, a medical instrument 10 of the present disclosure includes a guidewire 100 illustrated as being positioned within a conventional access or microcatheter 200. Such microcatheters are known in the art. Commercially available microcatheters include the Echelon™, Marathon™, and Nautica™ microcatheters sold by Tyco Healthcare Group, LP, dba Covidien, Irvine, Calif. In general, microcatheter 200 includes a handle 202 and an elongate flexible catheter member 204 extending from the handle 202. The catheter member 204 may be constructed of a cylindrical stock of one or more polymers, such as Grilamid brand polyamide/nylon from EMS Chemie, Switzerland, Pebax brand polyether/polyamide, from Actinofina Chemicals, France and the like. Microcatheter 200 defines a longitudinal opening or lumen 206 extending at least through the catheter member 204 for at least partial passage or reception of the guidewire 100.

Figure 2:
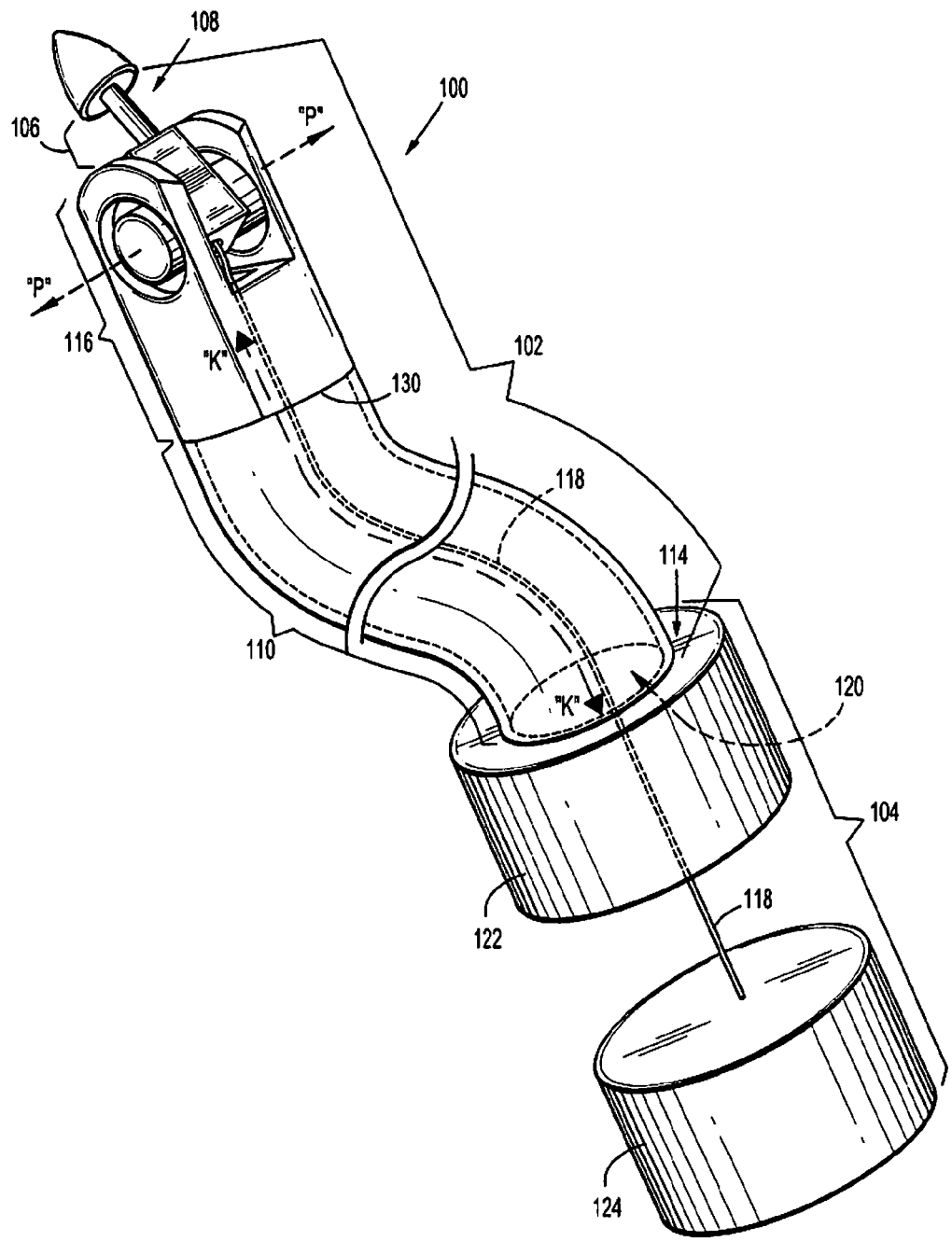
FIG. 2 is an enlarged perspective view of the guidewire of FIG. 1 illustrating an elongate guide member and an actuator assembly.

With reference to FIG. 2, guidewire 100 will be discussed. Guidewire 100 includes an elongate guide member 102 and an actuator assembly 104. The elongate guide member 102 is dimensioned for insertion within a body vessel of a subject, and defines a longitudinal axis "k." The elongate guide member 102 includes a leading tip segment 106 at a distal or leading end 108 thereof, an elongate body segment 110 extending to a proximal or trailing end 114 thereof, and an articulation joint 116 coupling the leading tip segment 106 to the elongate body segment 110. The articulation joint 116 defines a single axis "p" about which the leading tip segment 106 may be induced to articulate relative to the elongate body segment 110. A single elongate control element 118 extends through a longitudinal opening 120 of the elongate body segment 110, and is operatively coupled to the leading tip segment 106 and the actuator assembly 104. The control element 118 is longitudinally movable through manual manipulation of a clinician to cause corresponding articulating movement of the leading tip segment 106.

Since the leading tip segment 106 is pivotally connected to the elongate body segment 110 about the single axis "p," and since the leading tip segment 106 is operatively coupled to the single control element 118, the clinician is provided with a degree of certainty with respect to the manner in which the leading tip segment 106 will respond to manipulation of the actuator assembly 104.

The actuator assembly 104 of the guidewire 100 includes a first actuator 122 from which the elongate body segment 110 extends. First actuator 122 may incorporate various features (not depicted) including handles, slides or the like, to facilitate handling and/or movement of elongate guide member 102. Translational or longitudinal motion of the first actuator 122 may be transmitted to the elongate guide member 102. Also, rotational motion of the first actuator 122, e.g., rotational motion about the longitudinal axis "k" (see FIG. 2), may be transmitted to the elongate guide member 102.

The actuator assembly 104 also includes a second actuator 124 from which the control element 118 extends. As indicated above, the control element 118 extends from the second actuator 124 through the longitudinal opening 120 defined through the elongate body segment 110, and is operatively associated with the leading tip segment 106 of the elongate guide member 102. The second actuator 124 may be displaced longitudinally with respect to the first actuator 122 to impart a tensile or compressive force to the control element 118 and to impart a longitudinal displacement to the control element 118. The control element 118 may be constructed to transmit tensile and compressive loads from the second actuator 124 to the articulation joint 116. The control element 118 may exhibit an outer diameter in the range of about 0.001 inches to about 0.002 inches. The control element 118 may be a rod or shaft formed of a flexible material having sufficient rigidity to impart the articulating movement to the leading tip segment 106 as will be discussed. Suitable materials for the construction of the control element include metals such as stainless steel, tungsten, or nitinol, or non-metallic materials such as carbon fibers or polymeric materials.

Figure 3:
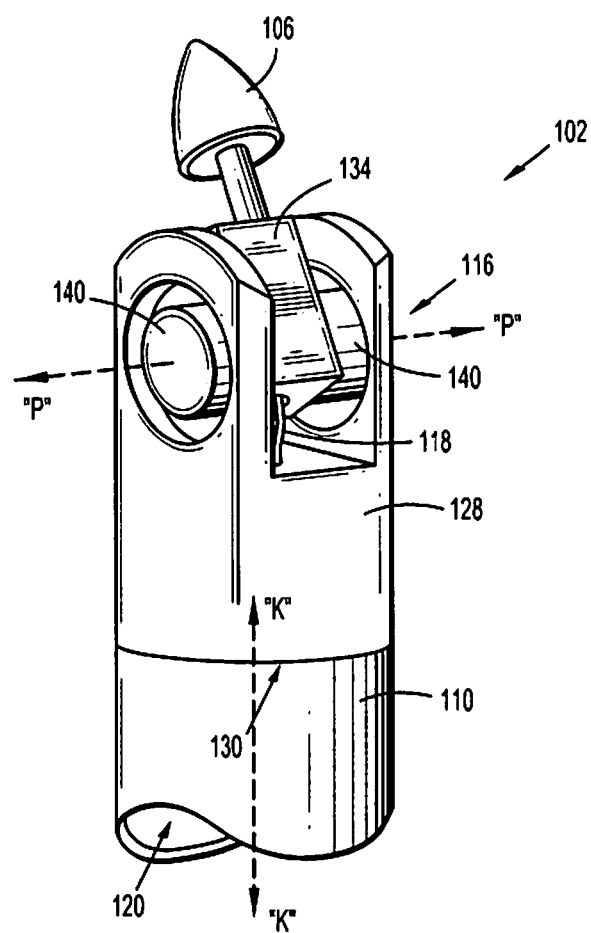
FIG. 3 is an enlarged perspective view of the elongate guide member of FIG. 2.

Referring now to FIG. 3, particulars of the elongate body segment 110, the articulation joint 116 and the leading tip segment 106 of the elongate guide member 102 will be discussed in greater detail. The leading tip segment 106, the articulation joint 116 and elongate body segment 110 are dimensioned for insertion within the vasculature and through the lumen 206 of the microcatheter 200 (FIG. 1). The elongate body segment 110 extends a substantial length of the elongate guide member 102 and may have a length ranging from about 20 cm to about 240 cm. The elongate body segment 110 may be generally circular in cross section with the longitudinal opening 120 extending at least along a major portion of the length of the elongate body segment 110. The elongate body segment 110 may be constructed of stainless steel, Nitinol, or another suitable alloy, which may provide the elongate body segment 110 with sufficient flexibility to navigate the vasculature. In other embodiments, longitudinal opening 120 may be constructed as a fold or tuck (not shown) formed in the elongate body segment 110 such that the longitudinal opening is disposed at least partially on an exterior of the elongate body segment 110.

A base 128 of the articulation joint 116 may be bonded to the elongate body segment 110 at bonding location 130. The elongate body segment 110 may exhibit an outer diameter in the range of about 0.011 inches to about 0.014 along a substantial length thereof, and the base 128 may exhibit a maximum lateral dimension no greater than the outer diameter of the elongate body segment 110 thus generally maintaining or corresponding to the profile of the elongated body segment 110. The entire elongate guide member 102 may be received in the lumen 206 of the microcatheter 200 (FIG. 1).

The articulation joint 116 pivotally connects the leading tip segment 106 to the elongate body segment 110 about the single pivot axis "p," which is transverse to the longitudinal axis "k." The base 128 maintains the pivot axis "p" in a stationary relationship with a leading end of the elongate body segment 110. The articulation joint 116 includes a pivoting member 134, which supports the leading tip segment 106 and is coupled to the control element 118. The leading tip segment 106 protrudes distally with respect to the elongate body segment 110 and the base 128, and defines a leading end of the elongate guide member 102. The pivoting member 134 is mounted to a pair of pivot bosses 140 extending into the base 128. In some embodiments, the pivoting member 134 and the pivot bosses 140 may be constructed monolithically as a single component. The pivot bosses 140 extend generally along the pivot axis "p," and, thus, the pivoting member 134 and the leading tip segment 106 are pivotally coupled to the base 128 about the pivot axis "p."

As depicted in FIG. 3, the leading tip segment 106 is constructed to exhibit a blunt, conical shape, but other atraumatic constructions may be provided such as coils, circular or oval cross section wire segments, or a flattened, planar or ribbon tips. As a further alternative (not shown), a leading tip segment may be heat set into a variety configurations including a linear arrangement or a bent "j-hook" as is known in the art, or, may be bent into a "j-hook" design by the clinician prior to the interventional procedure. For example, the leading tip segment 106 may range from about 5 cms to about 50 cms. The greatest cross-sectional lateral dimension or diameter of the leading tip segment 106 may be less than the lateral dimension of the articulation joint 116, or, in embodiments may approximate the lateral dimension of the articulation joint 116 to provide a smooth transition between the leading tip segment 106 and the articulation joint 116.

Referring now to FIGS. 4A to 4F, a method for manufacturing or assembling the elongate guide member 102 is described. Initially a stock material 144 (FIG. 4A) is provided with a pair of generally flat lateral faces 146 and a pair of curved faces 148. A curved surface 150 (FIG. 4B) may be micro-machined onto the stock material 144 on a leading side thereof. Next, an annular channel 152 (FIG. 4C) may be cut into each of the generally flat lateral faces 146. The annular channels 152 define the pivot bosses 140. A bore 154 may be drilled into the curved surface 150 to provide a connector for receiving leading tip segment 106. In other embodiments, a protrusion or snap-fit connector (not shown) may be provided to receive the leading tip segment 106. A cavity 156 may be cut out of a trailing side of the stock material 144 to provide passage of the control element 118, and an off-center bore 158 may be cut into a trailing surface of the cavity 156 to receive the control element 118. The off-center bore 158 is spaced radially with respect to the pivot axis "p" such that a torque may be generated about the pivot axis "p" by applying a longitudinal force to the pivoting member 134 at the off-center bore 158.

Next, parallel slots 160 (FIG. 4D) and a transverse slot 162 may be cut into stock material 146. The parallel slots 160 intersect the annular channels 152 and extend to the transverse slot 162. The transverse slot 162 extends through the stock material 146, and thus, the slots 160, 162 serve to separate the pivoting member 134 from the base 128. The base 128 retains the pivoting member 134 since the pivot bosses 140 protrude into the lateral faces 146 of the base 128. By micromachining the base 128 and the pivoting member 134 from the same stock material 146, no additional assembly of these two these components 128, 134 to one another is required. Thus, the pivot bosses 140 of the pivoting member 134 may extend to a full width of the base 128, and may be flush with the lateral faces 146. This construction provides a structurally strong articulation joint 116. This is particularly beneficial when for the relatively small diameter guidewires dimensioned for use within the neurovascular systems.

As indicated in FIG. 4E, the leading tip segment 106 may be received within the bore 154 and affixed to the pivoting member 134. Thus, the pivoting member 134 and the leading tip segment 106 may articulate together. The control element 118 may be received within the off-center bore 158 and may also be affixed to the pivoting member 134. Affixing the leading tip segment 106 and the control element 118 to the pivoting member 134 may be effected though the use of adhesives, welding, soldering or the like.

The base 128 may then be bonded to the elongate body segment 110 (FIG. 4F) coupling the articulation joint 116 to the elongate body segment 110. In other embodiments, the base 128 may be formed monolithically with a leading end of the elongate body segment 110.

The elongate guide member 102 including at least the elongate body segment 110 and/or the leading tip segment 106 may comprise a shape memory or superelastic alloy or polymer. One suitable shape memory alloy (SMA) or superelastic metal is Nitinol (NiTi), a nickel/titanium alloy, which is commercially available in various diameters or sizes. Superelastic alloys such as NiTi are relatively flexible capable of effectively tracking tortuous vasculature encountered while exhibiting advantageous restoration capabilities. Shape memory or superelastic metal or polymer such as NiTi may also be suitable for applications in which it is desired that leading tip segment 106 have a predetermined curvature. Shape memory alloys including NiTi can be heat set into a desired shape, straightened for delivery to a site, and then released to resume the heat-set shape. Other materials for the elongate guide member 102 may include an alloy consisting of Nickel, Titanium, and Cobalt commercially available from SAES Smart Materials, Inc, of New Hartford, N.Y.

It is further envisioned that a lubricious coating may be disposed over components of elongate guide member 102. Suitable lubricious coatings include hydrophilic materials such as polyvinylpyrrolidone (PVP), polyethylene oxide, polyethylene glycol, cellulosic polymers, and hydrophilic maleic anhydride, or hydrophobic materials such as silicone, PTFE, or FEP. These coatings are typically applied by dip coating or spray methods, and heat curing may be used. For example, cure temperatures up to about 70 degrees C. are used for silicone coatings, and several hundred degrees may be required for PTFE coatings. In addition to the lubricious coating, bioactive coatings may be applied over all or part of the guidewire. Such coatings also may incorporate materials such as heparin, hirudin and its analogs, or other drugs. These coatings typically are applied by dip coating. Bioactive coatings are desirable to prevent blood clotting or for delivery of drugs to a specific site.

Figure 6:
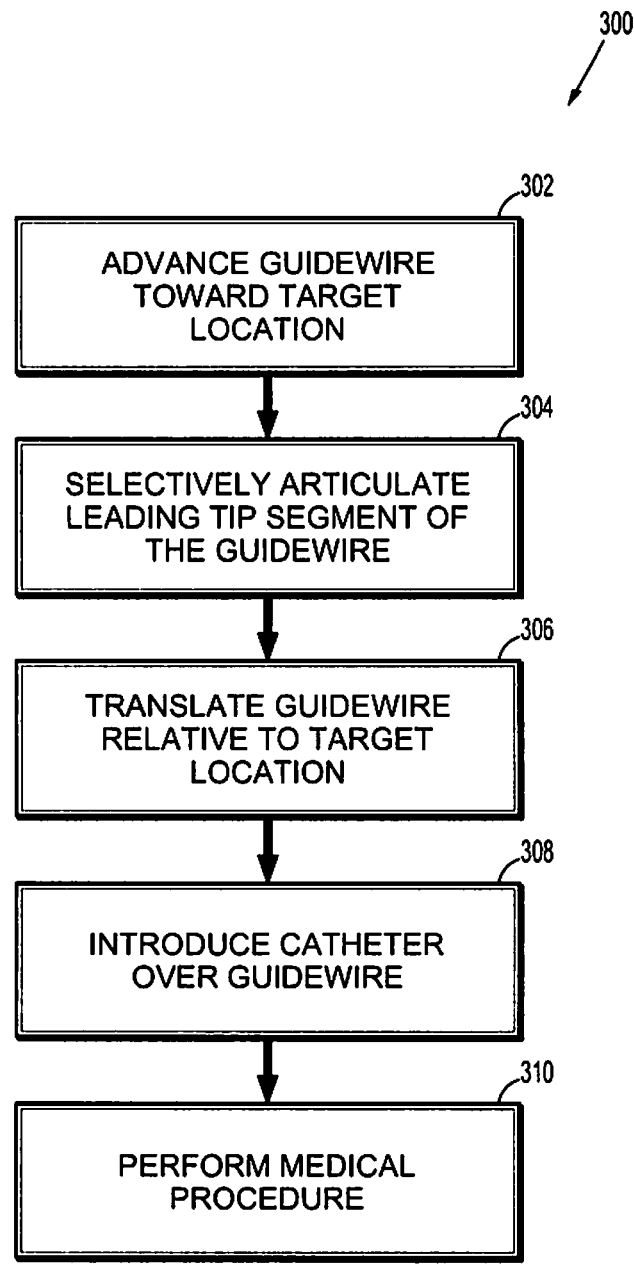
FIG. 6 is a flow chart illustrating a methodology for performing a medical procedure with the guidewire.

Referring now to FIGS. 1, 5A and 5B, in conjunction with the flow chart of FIG. 6, usage of the guidewire 100 in connection with performing a medical procedure 300 (FIG. 6) will be described. The actuator assembly 104 may be operated to position the elongate guide member 102 in the neurovascular space "n" (FIG. 1). A clinician may translate the first actuator 122 to advance the elongate guide member 102 to a target location, e.g., a juncture in the vasculature. (STEP 302) The clinician may rotate the first actuator 122 to orient the leading end 108 of the elongate guide member 102 with respect to the neurovascular space "n." For example, a clinician may rotate the first actuator 122 in the direction of arrow "a" (FIG. 1) through an angle "α" to cause a corresponding rotation of the leading end 108 of the elongate guide member 102 in the direction of arrow "A" through an angle θ within the vasculature.

Also, if necessary, the clinician may operate the second actuator 124 to articulate the leading tip segment 106 (STEP 304) with respect to the elongate body segment 110 (FIGS. 5A and 5B) such that further translation of the elongate guide member 102 will direct the leading end 108 of the elongate guide member 102 into the intended vessel, e.g., vessel "v2" (STEP 306). For example, a clinician may pull the second actuator 124 in the direction of arrow "b" to apply a tensile force to the control element 118. Since the control element 118 is coupled to the pivoting member 134 at a location offset from the pivot axis "p," the tensile force in the control element 118 causes the pivoting member 134 and the leading tip segment 106 to pivot in the direction of arrow "B." In some embodiments, the control element 118 may be sufficiently rigid such that a compressive force may be imparted thereto to induce pivotal movement of the pivoting member 134 and the leading tip segment 106 in a direction opposite the direction of arrow "B." This articulating motion may be effected without translating the leading end 108 of the elongate guide member 102. For example, the second actuator 124 may longitudinally move or translate relative to the first actuator 122 to effect angulation of the leading tip segment 106. The independency of these motions may facilitate predictability with respect to placement and positioning of the leading tip segment 106 relative to vessel "v2", and assist the clinician in achieving the intended orientation of the leading tip segment 106.

The size of the articulation joint 116 may be relatively small with respect to the second actuator 124. Thus, second actuator 124 may be extremely sensitive. For example, a very small movement of the second actuator 124 in the direction of arrow "b" may be sufficient to move the pivoting member 134 and the leading tip segment 106 in the direction of arrow "B." Since the leading tip segment 106 is pivotally connected to the elongate body segment 110 about the single axis "p" and the pivot bosses 140, the clinician is provided with a degree of certainty with respect to the manner in which the leading tip segment 106 will respond to manipulation of the actuators 122, 124.

Once the guidewire 100 is positioned as desired relative to the target location within the neurovascular space "n," the catheter member 204 of the microcatheter 200 may be advanced over the elongate guide member 102 of the guidewire 100 to position the microcatheter 200 within the neurovascular space "n" adjacent the target location (STEP 308). The microcatheter 200 may then be used to perform a medical procedure (STEP 310) including treatment of an aneurysm or an arterio-venous malformation, performing an angioplasty or stenting. In some other procedures, the catheter member 204 or another device (not shown) may be initially positioned on the elongate guide member 102, and positioned within the neurovascular space "n" along with the guidewire 100.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A guidewire for use in a medical procedure, which comprises:
    an elongate guide member dimensioned for insertion within a body vessel of a subject, the elongate guide member defining a longitudinal axis and having leading and trailing ends, the elongate guide member including an elongate body segment and a leading tip segment, the elongate body segment defining a longitudinal opening and the leading tip segment being adapted and dimensioned to articulate relative to the elongate body segment about a single axis of articulation;
    a control element extending through the longitudinal opening of the elongate body segment and operatively coupled to the leading tip segment, the control element longitudinally movable to cause corresponding articulating movement of the leading tip segment about the single axis of articulation;
    a first actuator coupled to the guide member for imparting at least rotational movement to the guide member; and
    a second actuator coupled to the control element, the second actuator adapted for sliding longitudinal movement in a direction generally parallel to the longitudinal axis and independently movable relative to the first actuator to cause corresponding movement to the control element and articulating movement of the leading tip segment about the single axis of articulation.

2. The guidewire according to claim 1 wherein the guide member includes an articulation joint for coupling the leading tip segment to the elongate body segment.

3. The guidewire according to claim 2 wherein the articulation joint includes:
    a base coupled to the elongate body segment; and
    a pivoting member mounted to the base, the pivoting member coupled to the leading tip segment and to the control element, the pivoting member adapted to pivot relative to the base and about the single axis of articulation in response to longitudinal movement of the control element to thereby cause corresponding pivoting movement of the leading tip segment.

4. The guidewire according to claim 3 wherein the control element is connected to the pivoting member at a location spaced from the single axis of articulation.

5. The guidewire according to claim 4 wherein the pivoting member defines an off-center bore spaced from the single axis of articulation for receiving a leading end of the control element.

6. The guidewire according to claim 1 wherein the control element consists of a single control element.

7. The guidewire according to claim 6 wherein the second actuator is coupled to the single control element such that longitudinal movement of the second actuator in a first direction applies a tensile force to the single control element causing the leading tip segment to pivot in a first direction and longitudinal movement of the second actuator in a second direction applies a compressive force to the single control element causing the leading tip segment to pivot in a second direction opposite the first direction.

8. A guidewire for use insertion within vasculature of a subject, which comprises:
 an elongate guide member dimensioned for insertion within vasculature of a subject, the elongate guide member defining a longitudinal axis and having leading and trailing ends, the elongate guide member including an elongate body segment and a leading tip segment, the elongate body segment defining a longitudinal opening and the leading tip segment being adapted and dimensioned to articulate relative to the elongate body segment about a single axis;
 a control element extending through the longitudinal opening of the elongate body segment and operatively coupled to the leading tip segment, the control element longitudinally movable through manual manipulation of a clinician;
 a base coupled to the elongate body segment;
 a pivoting member mounted to a pivot boss, the pivot boss extending generally along the single axis, and coupled to the base, the pivoting member coupled to the leading tip segment and to the control element, the pivoting member adapted to pivot relative to the base via the pivot boss and about the single axis in response to longitudinal movement of the control element to thereby cause corresponding pivoting movement of the leading tip segment about the single axis;
 a first actuator coupled to the guide member for imparting at least rotational movement to the guide member; and
 a second actuator coupled to the control element, the second actuator adapted for sliding longitudinal movement in a direction generally parallel to the longitudinal axis and relative to the first actuator to cause corresponding movement to the control element and articulating movement of the leading tip segment relative to the base and about the single axis.

9. The guidewire according to claim 8 wherein the elongate body segment of the elongate guide member and the control element are generally flexible.

10. The guidewire according to claim 8 wherein the control element consists of a single control element.

11. An intravascular guidewire and microcatheter system, which comprises:
 an elongate guide member dimensioned for insertion within a body vessel of a subject, the elongate guide member defining a longitudinal axis and having leading and trailing ends, the elongate guide member including an elongate body segment and a leading tip segment, the leading tip segment being adapted and dimensioned to pivot movement relative to the elongate body segment;
 a control element operatively coupled to the leading tip segment, the control element longitudinally movable through manual manipulation of a clinician to cause corresponding pivoting movement of the leading tip segment;
 a handle connected to the control element, the handle adapted for longitudinal movement in a direction generally parallel to the longitudinal axis to cause corresponding longitudinal movement of the control element; and
 a microcatheter defining a lumen receiving the elongated guide member.

12. The system according to claim 11 wherein the leading tip segment is adapted to pivot about a single pivot axis.

13. The system according to claim 12 wherein the control element is operatively coupled to the leading tip segment at a location radially spaced from the single pivot axis.

14. The system according to claim 13 wherein the elongate body segment defines a longitudinal opening, the control element being at least partially disposed within the longitudinal opening and adapted for reciprocal longitudinal movement therewithin to cause corresponding pivotal movement of the leading tip segment.

15. The system according to claim 12 including an articulation joint for coupling the leading tip segment to the elongate body segment, the articulation joint dimensioned and adapted to enable pivotal movement of the leading tip segment relative to the elongate body segment.

16. The system according to claim 15 wherein the articulation joint includes a pivoting member, the pivoting member coupled to the leading tip segment and to the control element, the pivoting member adapted to pivot about the single pivot axis in response to longitudinal movement of the control element to thereby cause corresponding pivoting movement of the leading tip segment.

17. The system according to claim 16 wherein the articulation joint includes a base, the base coupled to the elongate body segment and having the pivoting member pivotally mounted thereto.

18. The guidewire according to claim 11 including an actuator coupled to the guide member for imparting at least rotational movement to the guide member, the handle being movable independent of the actuator.

19. The guidewire according to claim 11 wherein the control element consists of a single control element.

20. A method for performing a medical procedure within a body lumen, comprising the steps of:
 advancing a guidewire through a vasculature toward a target location;
 selectively articulating a leading tip segment adjacent a leading end of the guidewire by longitudinally moving a control consisting of a single control element connected to the leading tip segment through manual manipulation by a clinician to pivot the leading tip segment about a single pivot axis and about a pivot boss operatively connecting the leading tip segment to a trailing segment of the guidewire to achieve a desired orientation of the leading tip segment with respect to the target location;
 introducing a catheter over the guidewire; and
 performing a medical procedure within the target location with the catheter.

21. The method according to claim 20 including, subsequent to the step of selectively articulating the leading tip segment, the step of further translating the guidewire to direct the leading end of the guidewire within the target location.

22. The method according to claim 21 wherein the step of advancing the guidewire includes manually manipulating a first actuator of the guidewire.

23. The method according to claim 22 wherein the step of manually manipulating the first actuator includes rotating the first actuator to cause corresponding rotation of the leading end for arranging with respect to the target location.

24. The method according to claim 23 wherein the step of selectively articulating the leading tip segment includes manually manipulating a second actuator of the guidewire.

25. The method according to claim 24 wherein the second actuator is operatively connected to the single control element and to the leading tip segment, whereby the step of selectively articulating the leading tip segment includes longitudinally moving the second actuator relative to the first actuator to effect corresponding articulating movement of the leading tip segment.

26. A guidewire for use in a medical procedure, which comprises:

an elongate guide member dimensioned for insertion within a body vessel of a subject, the elongate guide member defining a longitudinal axis and having leading and trailing ends, the elongate guide member including an elongate body segment and a leading tip segment, the elongate body segment defining a longitudinal opening, the leading tip segment being adapted and dimensioned for articulating movement relative to the elongate body segment, the articulating movement consisting of pivotal movement about a single axis of articulation;

a control extending through the longitudinal opening of the elongate body segment and operatively coupled to the leading tip segment, the control longitudinally movable to cause corresponding articulating movement of the leading tip segment; and a handle coupled to the control, the handle adapted for sliding longitudinal movement in a direction generally parallel to the longitudinal axis of the guide member to cause corresponding movement to the control element and articulating movement of the leading tip segment.

27. The guidewire according to claim 26 wherein the control is a single control element.

28. The guidewire according to claim 26 wherein the single axis of articulation is a fixed axis.

* * * * *